United States Patent [19]

Hirao et al.

[11] 3,994,882
[45] Nov. 30, 1976

[54] NITROFURAN DERIVATIVES, PROCESS FOR THE PREPARATION THEREOF AND COMPOSITIONS CONTAINING SAME AS ACTIVE INGREDIENT

[75] Inventors: Ichiro Hirao, Kitakyushu; Ryuzo Ueno, Nishinomiya, both of Japan

[73] Assignee: Kabushiki Kaisha Ueno Seiyaku Oyo Kenkyujo, Japan

[22] Filed: Sept. 10, 1974

[21] Appl. No.: 504,987

[30] Foreign Application Priority Data

July 22, 1974 Japan.................................. 49-83285

[52] U.S. Cl............................. 260/240 A; 424/285
[51] Int. Cl.²....................................... C07D 307/72
[58] Field of Search............... 260/240, 80, 240 A, 260/240 D

[56] References Cited
UNITED STATES PATENTS

| | | | |
|---|---|---|---|
| 3,066,167 | 11/1962 | Horrom | 260/518 |
| 3,468,952 | 9/1969 | Ehrhart et al. | 260/518 |
| 3,484,481 | 12/1969 | Obendorf et al. | 260/518 |
| 3,532,691 | 10/1970 | Haack et al. | 260/240 A |
| 3,542,928 | 11/1970 | Elliott et al. | 424/285 |
| 3,709,938 | 1/1973 | Houlihan | 260/518 |
| 3,780,095 | 12/1973 | Klemm et al. | 260/518 |

FOREIGN PATENTS OR APPLICATIONS 44-13505 6/1969 Japan............................. 260/240 A

OTHER PUBLICATIONS

Kitamura et al., Nippon Kagaku Zasshi, vol. 87, pp. 1063–1069 (1966).

*Primary Examiner*—John D. Randolph
*Attorney, Agent, or Firm*—Wenderoth, Lind & Ponack

[57] ABSTRACT

A nitrofuran derivative having the general formula

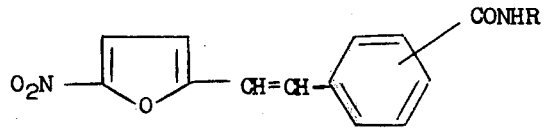

wherein R is a group selected from the class consisting of hydroxyl group, hydroxyalkyl group, hydroxyalkoxylakyl group, hydroxyalkylaminoalkyl group, alkoxyalkyl group, sulfoalkyl group, which sulfoalkyl group may be that forming a salt, mercaptoalkyl group, an amino acid, and a residue resulting from the removal of the amino group from an amino acid amide, the amino group or carboxyl group of which residue may be that forming a salt. The nitrofuran derivative is useful as antimicrobial agent.

16 Claims, No Drawings

NITROFURAN DERIVATIVES, PROCESS FOR THE PREPARATION THEREOF AND COMPOSITIONS CONTAINING SAME AS ACTIVE INGREDIENT

This invention relates to a novel nitrofuran derivative, a process for the preparation thereof and compositions which contain such nitrofuran derivative as active ingredient, which compositions are for use of man, animals other than man, or fish in preventing or curing disorders caused by microorganisms.

Para-[2-(5'-nitro-2'-furyl)-vinyl]-benzoylamine

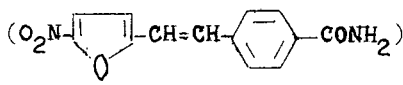

is mentioned in Nippon Kagaku Zasshi (Journal of the Chemical Society of Japan) vol. 87, pp. 1063 – 1069 (1966) and is also referred to as 5-nitro-2-(p-carbomoylstyryl)-furan. This compound (A) demonstrates extremely superior antimicrobial activity in vitro, and it is especially effective in inhibiting the growth of *Streptococcus hemolyticus, Staphylococcus aureus, Escherichia coli* and salmonella species, etc., at a low concentration of 0.1-3 micrograms per milliliter. However, the concentration in blood of this compound can scarcely be noted, and since its in vivo antimicrobial activity is not observed, it is entirely unsuitable for use as a chemotherapeutic agent for man as well as a medicine for animals other than man.

In consequence of our researches into new nitrofuran derivatives that would be effective for such purposes as mentioned above, in which researches attempts at synthesis of various substituted compounds having substituents at the amino group of compound (A) were made and the properties thereof were studied, we found as an acid amide derivative a new secondary acid amide derivative having a hydroxyl group or carboxyl group etc. exhibited very superior antimicrobial activity in vivo.

There are provided according to this invention nitrofuran derivatives of the general formula

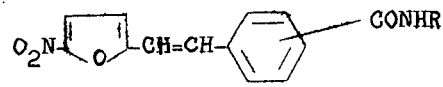

wherein R is a group selected from the class consisting of hydroxyl group, hydroxyalkyl group, hydroxyalkoxyalkyl group, hydroxyalkylaminoalkyl group, alkoxyalkyl group, sulfoalkyl group, which sulfoalkyl group may be that forming a salt, mercaptoalkyl group, an amino acid, and a residue resulting from the removal of the amino group from an amino acid amide, the amino group or carboxyl group of which residue may be that forming a salt.

In the foregoing general formula, R is preferably a group selected from the class consisting of one hydroxyl group, a hydroxyalkyl group containing 1–5 hydroxyl, an alkoxyalkyl group containing one hydroxyl, a hydroxyalkylaminoalkyl group containing one hydroxyl, an alkoxyalkyl group, a sulfoalkyl group containing one sulfo, which sulfoalkyl group may be that forming a salt with an inorganic base, a mercaptoalkyl group containing one mercapto, and an alpha-amino acid selected from the group consisting of alanine, arginine, aspartic acid, asparagine, cysteine, cystine, glutamic acid, glutamine, glycine, histidine, hydroxylysine, isoleucine, leucine, lysine, methionine, phenylalanine, serine, threonine, tryptophan, tyrosine and valine, and a residue resulting from the removal of the amino group from the alpha-amino acid amide, the amino group of which residue may be that forming an acid addition salt with a mineral acid, or the carboxyl group of which residue may be that forming a salt with an inorganic base; the alkyl and alkoxy radicals of which groups are of 1–6 carbon atoms.

More preferably R is a member selected from the class consisting of one hydroxyl group, a hydroxyalkyl group containing 1–3 hydroxyl, an alkoxyalkyl group containing one hydroxyl, a hydroxyalkylaminoalkyl group containing one hydroxyl, an alkoxyalkyl group, a sulfoalkyl group containing one sulfo, which sulfoalkyl group may be that forming a salt of an alkali metal or alkaline earth metal, a mercaptoalkyl group containing one mercapto, and an amino acid selected from the group consisting of alanine, arginine, aspartic acid, asparagine cysteine, cystine, glutamic acid, glutamine, glycine, oxylysine, isoleucine, leucine, lysine, methionine, serine, threonine and valine, or a residue resulting from the removal of the amino group from the alpha-amino acid, amides, the amino group of which residue may be that froming an acid addition salt with a hydrohalogenic acid, sulfuric acid or phosphoric acid, and the carboxyl group of which residue may be that forming a salt of an alkali metal or alkaline earth metal; the alkyl and alkoxy radicals of which groups are of 1–4 carbon atoms.

Still more preferably R is a member selected from the class consisting of one hydroxyl group, a hydroxyalkyl group containing 1–3 hydroxyl, the alkyl portion of which contains 1–4 carbon atoms, a hydroxyalkoxyalkyl group containing one hydroxyl, the alkyl portion of which contains 1–2 carbon atoms and the alkoxy portion of which contains 1–3 carbon atoms, a hydroxyalkylaminoalkyl group containing one hydroxyl, the hydroxyalkyl portion of which contains 1–3 carbon atoms and the aminoalkyl portion of which contains 1–2 carbon atoms, an alkoxyalkyl group containing one hydroxyl, the alkoxy portion of which contains 1–3 carbon atoms and the alkyl portion of which contains 1–3 carbon atoms, a sulfoalkyl group containing one sulfo, the alkyl portion of which contains 1–2 carbon atoms, which sulfoalkyl group may be that forming a sodium or potassium salt, a mercaptoalkyl group containing one mercapto, the alkyl portion of which contains 1–2 carbon atoms, and an alpha-amino acid selected from the group consisting of arginine, asparagine, glycine and serine, or a residue resulting from the removal of the amino group from an alpha-amino acid amide selected from the group consisting of glycine amide and serine amide, the amino group of which residue may be that forming an addition salt with hydrochloric acid or hydrobromic acid, or the carboxyl group of which residue may be that forming a sodium or potassium salt.

Of the compounds of the present invention having the foregoing channel formula I, preferred are, in general, the nitrofuran derivatives having the formula

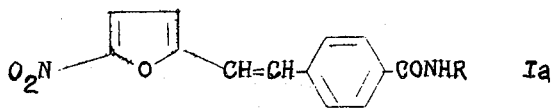

wherein R is as above defined, i.e., the nitrofuran derivatives in which the RHNCO- group is attached in a position para to the 5-nitro-2-furyl-vinyl group in the benzene ring.

Especially preferred nitrofuran derivatives include 2-para-[2'-(5''-nitro-2''-furyl)-vinyl]-benzoylamino-ethanol, 2-meta-[2'-(5''-nitro-2''-furyl)vinyl]-benzoylamino-ethanol, 3-para-[2'-(5''-nitro-2''-furyl)-vinyl]-benzoylamino-1-propanol, 3-para-[2'-(5''-nitro-2''-furyl)-vinyl]-venzoylamino-2-propanol, 3-para-[2'-(5''-nitro-2''-furyl)-vinyl]-venzoylamino-1,2-propanediol, 2-para-[2'-(5''-nitro-2''-furyl)-vinyl]benzoylaminoethoxy-2-ethanol, para-[2-(5'-nitro-2'-furyl)vinyl]-N-benzoylglycine amide, and para-[2-(5'-nitro-2'-furyl)vinyl]-N-benzoylserine amide.

There is provided in accordance with this invention a process for preparing the nitrofuran derivatives having the general formula

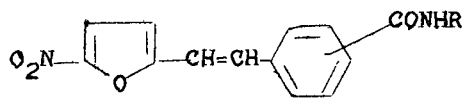

I wherein R is as hereinbefore defined, which comprises reacting a 2-(5'-nitro-2'-furyl)-vinyl-benzoyl halide having the general formula

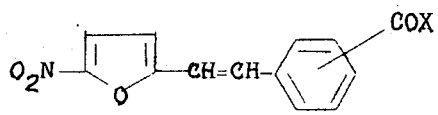

II wherein X is halogen, with an amine derivative having the general formula

NH$_2$R    III wherein R is an above defined.

As the 2-(5'-nitro-2'furyl)-vinyl-benzoyl halide of the above general formula II, the ortho- mta- or para-[2-(5'-nitro-2'-furyl)-vinyl]-benzoyl halide can be used, the chlorides being preferred.

As the amine derivatives of the foregoing general formula III, usable are the amine derivatives having the above-defined R. As preferred amine derivatives, mention can be made of such compounds as follows: when R is a hydroxyl group, hydroxylamine, when R is a hydroxyalkyl group, e.g., monoethanolamine, monopropanolamide, monobutanolamine, aminopropanediol, aminobutanediol and aminobutanetriol, when R is a hydroxyalkoxyalkyl group, e.g., hydroxyethoxyethylamine and hydroxypropoxyethylamine, when R is a hydroxyalkylaminoalkyl group, e.g., hydroxyethylaminoethylamine and hydroxypropylaminoethylamine, when R is an alkoxyalkyl group, e.g., methoxypropylamine and propoxypropylamine, when R is a sulfoalkyl group, e.g., sulfoethylamine, and when R is a mercaptoalkyl group, e.g., mercaptoethylamine. On the other hand, as the amino acids or amino acid amides having the above-defined R, when there are isomers, any of the isomers can be used, for example, either the D, L, or DL form may be used. Preferred are the alpha-amino acids or alpha-amino acid amides. Especially preferred amino acid amides include, for example, glycine, glycine amide, lysine, arginine, glutamine, asparagine, serine and serine amide. The free amino group of the amino acid or amino acid amide may be that forming an acid addition salt with a mineral acid (e.g., hydrochloric acid, hydrobromic acid, hydroiodic acid or sulfuric acid) or an organic acid (e.g., acetic acid, citric acid or p-toluenesulfonic acid). On the other hand, the free carboxyl group of the foregoing acid or acid amide may be that forming a salt of an alkali metal or alkaline earth metal (e.g., potassium, sodium or calcium). In the case where the free amino group is that froming an acid addition salt, as indicated above, it is necessary to add a hereinafter indicated dehydrohalogenating agent in at least an amount equimolar to that of the acid forming the acid addition salt. Again, the free amino group of the amino acid or amino acid amide may also be protected by a customary protective group (e.g., benzylidene, isopropylidene or furfurylidene).

In the reaction of the present invention a 2-(5'-nitro-2'-furyl)-vinyl-benzoyl halide of the general formula II and an amine derivative of the general formula III are reacted in stoichiometric amounts. Now, in this case it is possible to use as the dehydrohalogenation agent an excess of the foregoing amine derivative (not forming an acid addition salt). In the instant reaction it is preferred to use an excess of the aforesaid amine derivative as indicated above, inorganic bases such as the alkali hydroxides (e.g., sodium hydroxide and potassium hydroxide), the alkali carbonates (e.g., sodium carbonate and potassium carbonate) and the alkali hydrogencarbonates (e.g., sodium hydrogencarbonate and potassium hydrogencarbonate), and organic bases such as triethylamine, pyridine, quinoline and methylaniline.

The instant reaction is suitably carried out under reaction conditions in an inert organic solvent, for example, such ethers as ethyl ether, dioxane and tetrahydrofuran, such halogenated hydrocarbons as trichloroethylene, chloroform and chlorobenzene, and such hydrocarbons as benzene, toluene, xylene, cyclohexane and petroleum benzine. For instance, the 2-(5'-nitro-2'-furyl)-vinyl-benzoyl halide may be dissolved or suspended in an inert organic solvent such as described above followed by the addition thereto of the amine derivative. Alternately, the foregoing organic solvent may be dispensed with and the 2-(5'-nitro-2'-furyl)-vinyl-benzoyl halide be added to an aqueous solution of the amine derivative.

While the 2-(5'-nitro-2'-furyl)-vinyl-benzoyl halide may be used in its isolated state, it is also possible to use that prepared in customary manner from 2-(5'-nitro-2'-furyl)-vinyl-benzoic acid, in its as-obtained state without isolation.

The reaction temperature is preferably not too high. The reaction usually proceeds smoothly at a temperature ranging from −30° to +70° C., and preferably from 0° to 50° C.

The resulting nitrofuran derivatives of the formula I can be isolated and purified in customary manner On the resulting nitrofuran derivatives of the general formula I, those whose R is a sulfoalkyl group or a residue resulting from the removal of the amino group from the amino acid or amino acid amide and containing a free carboxyl group can be transformed their sulfo or carboxyl group in customary manner into a nontoxic sodium, potassium or calcium salt by the use of, say, an inorganic base (e.g., an alkali metal or alkaline earth metal hydroxide, carbonate or hydrogencarbonate such as sodium hydroxide, potassium hydroxide, calcium hydroxide, sodium carbonate, sodium hydrogencarbonate, potassium hydrogencarbonate and potassium carbonate) or an alkali alcoholate (e.g., sodium alcoholate or potassium alcoholate). On the other hand, of the resulting nitrofuran derivatives of the general formula I, those whose R is a residue resulting from the removal of the amino group from the amino acid or amino acid amide and containing a free amino group can be transformed in customary manner into a salt, say an addition salt with a mineral acid (e.g., the hydrohalogenated salts such as hydrochlorides, hydrobromides and hydroiodides, and sulfates or phosphates).

The invention nitrofuran derivatives of the general formula I demonstrate excellent antimicrobial activity against microorganisms, for example, the gram-positive microorganisms such as *Streptococcus hemolyticus*, *Staphylococcus aureus*, and *Diplococcus pneumoniae* as well as the gram-negative microorganisms such as *Escherichia coli* and the salmonella species. The minimum growth inhibiting concentrations ($\mu$g/ml) (MIC) of typical nitrofuran derivatives will be shown in the following Tables 1–3.

Table 1

MINIMUM GROWTH INHIBITING CONCENTRATIONS ($\mu$g/ml)

$$O_2N\text{-furan-}CH=CH\text{-phenyl-}CONHR$$

| Example | Compound —CONHR | Diplococcus pneumoniae DP-1 | Streptococcus hemolyticus A 089 | Staphylococcus aureus 209P | Bacillus Subtilis PCI219 | Salmonella enteritidis 1891 | Salmonella pullorum chuyu 114 | Escherichia coli O-55 | Klebsiella pneumoniae ST-101 | Proteus vulgaris HX-19 | Pseudomonas aeruginosa 347 |
|---|---|---|---|---|---|---|---|---|---|---|---|
| 1 | p-CONH—CH$_2$CH$_2$OH | 0.78 | <0.19 | 0.78 | <0.19 | 1.56 | 3.13 | 3.13 | 3.13 | 3.13 | 12.5 |
| 2 | m-CONH—CH$_2$CH$_2$OH | <0.19 | <0.19 | 0.78 | <0.19 | 0.78 | 3.13 | 3.13 | 1.56 | 6.25 | 25 |
| 4 | p-CONH—CH$_2$CH$_2$CH$_2$OH | 6.25 | <0.19 | 0.78 | <0.19 | 3.13 | 6.25 | 3.13 | 3.13 | 6.25 | >25 |
| 5 | p-CONH—CH$_2$CHCH$_3$ \| OH | 0.78 | 0.19 | 0.78 | <0.19 | 1.56 | 6.25 | 6.25 | 3.13 | 3.13 | >25 |
| 9 | p-CONH—CH$_2$CH—CH$_2$ \| \| OH OH | <0.19 | <0.19 | 0.78 | <0.19 | 1.56 | 6.25 | 3.13 | 6.25 | 6.25 | >25 |
| 11 | p-CONH—CH$_2$CH$_2$OCH$_2$CH$_2$OH | 0.78 | <0.19 | 1.56 | <0.19 | 1.56 | 6.25 | 6.25 | 3.13 | 6.25 | 25 |
| 16 | p-CONH—CH$_2$CONH$_2$ | 0.39 | <0.19 | 0.78 | <0.19 | 0.78 | 3.13 | 3.13 | 3.13 | 3.13 | >25 |
| 19 | p-CONH—CHCONH$_2$ \| CH$_2$OH | 0.78 | <0.19 | 1.56 | <0.19 | 1.56 | 6.25 | 12.5 | 6.25 | 6.25 | 25 |

For information, the minimum growth inhibiting concentration is a value concerning microorganisms cultivated in TSBI the pH of which was adjusted to 7.2, each bacteria being incubated at 37° C. for 48 hours.

Table 2

MINIMUM GROWTH INHIBITING CONCENTRATIONS ($\mu$g/ml)
(Microorganisms that infect domestic animals)

| Example | Compound —CONHR | Salmonella purollum 42 strains | Escherichia coli 36 strains | Mycoplasma gallisepticum 6 strains | Staphylococcus aureus 15 strains | Hemophilus galinalum 2 strains | Bordetella bronchiseptica 4 strains | Pasteurella multocida Kobe-5 | Erysipelothrix rhusiopatiae Agata |
|---|---|---|---|---|---|---|---|---|---|
| 1 | p-CONH—CH$_2$CH$_2$OH | 1.6–12.5 | 0.5–25.0 | 0.1 | 0.2–25.0 | 0.04–1.5 | 25.0 | 0.15 | 0.07 |
| 9 | p-CONH—CH$_2$CH—CH$_2$ \| \| OH OH | 1.6–25.0 | 0.5–12.5 | 0.2 | 0.2–25.0 | 0.1–1.5 | 25.0 | 0.08 | 0.15 |
| | Culture medium | TSB-Agar | ″ | Hofstad* | TSB-agar | TSB-Agar 10% rabbit blood added | Heart infusion -Agar | TSB-Agar 10% rabbit blood added | ″ |

The minimum growth inhibiting concentrations were measured under identical conditions as in the case of Table 1, except that culture media indicated above were used and, in the case of that asterisked, the culture was carried out for 5 days, while the others were cultivated for 48 hours.

Table 3

MINIMUM GROWTH INHIBITING CONCENTRATIONS ($\mu$g/ml)
(Microorganisms that infect fish)

| Example | Compound —CONHR | Aero-monas punctata | Aero-monas lique-faciens | Aero-monas sal-monicida | Vibrio piscium var. Japonicus | Vibrio anguil-larum K-3 | Vibrio panulirus Vp-M-1 | Vibrio sp. Sp-1 | Chondro-coccus co-lumnaris Ek-23 | Pasteure la piricida SU |
|---|---|---|---|---|---|---|---|---|---|---|
| 1 | —CONH CH$_2$CH$_2$OH | 0.125 | 0.062 | 0.018 | <0.015 | 0.018 | 0.009 | 0.018 | 0.0037 | 0.037 |
| 9 | —CONH CH$_2$—CH—CH$_2$ $\quad\;$ \|  $\;\;$ \| $\quad\;$ OH  OH | 0.25 | 0.037 | 0.018 | <0.015 | 0.037 | 0.009 | 0.018 | 0.0037 | 0.037 |
| Culture medium | | 0.5% NaCl added ordinary agar | '' | '' | '' | 3% NaCl added ordinary agar | '' | '' | 0.5% NaCl added TSB agar | * 2% NaCl added brain-heat infusion agar |

The minimum growth inhibiting concentrations were measured under indentical contitions as in the case of Table 1. The culture temperature was 25° C., the culture being carried out for 48 hours in the asterisked case and 24 hours in the other cases.

Next, in Table 4 are shown the curative actions (ED$_{50}$ mg/Kg body wt.) and acute toxicities (LD$_{50}$ mg/kg body wt.) of the typical nitrofuran derivatives of the present invention when used with infected mice.

tory curative actions were demonstrated when they were administered to infected mice, whereas no curative effects were noted in the case of the compound A, and there were cases where this effect was superior to the conventional antibiotics depending upon the compound.

Hence, the nitrofuran derivatives of the general formula I of this invention are suitably used as a chemotherapeutic agent for the prevention or thereby of the Table 4

CURATIVE ACTION (ED$_{50}$ mg/kg body wt.) AND ACUTE TOXICITY (LD$_{50}$ mg/kg body wt.) WHEN ADMINISTERED TO INFECTED MICE

| | Compound | ED$_{50}$ (mg/kg body wt.) | | | | |
|---|---|---|---|---|---|---|
| | | 1) | 2) | 3) | 4) | |
| Example | —CONHR | Streptococcus hemolyticus A 089 | Staphylo-coccus aureus 72r | Escherichia coli K-74 | Salmonella typhimium K-52 | LD$_{50}$ (mg/kg body wt.) |
| 1 | P-CONH CH$_2$CH$_2$OH | 8 | 14 | 14 | 75 | 1500 |
| 2 | m-CONH CH$_2$CH$_2$OH | 34 | 37 | 45 | 150 | 2000 |
| 4 | p-CONH CH$_2$CH$_2$CH$_2$OH | 24 | 50 | — | 125 | 1900 |
| 5 | p-CONH CH$_2$CHCH$_3$ $\quad\quad$ \| $\quad\quad$ OH | 19 | 37 | — | 110 | 1700 |
| 9 | p-CONH CH$_2$—CH—CH$_2$ $\quad\;$ \|  $\;\;$ \| $\quad\;$ OH  OH | 15 | 21 | 10 | 100 | >2000 |
| 11 | p-CONH CH$_2$CH$_2$OCH$_2$CH$_2$OH | 13 | 21 | 29 | 100 | 1850 |
| 16 | p-CONH CH$_2$CONH$_2$ | 34 | 30 | 34 | 110 | 2000 |
| 19 | p-CONH CHCONH$_2$ $\quad$ \| $\quad$ CH$_2$OH | 46 | 65 | — | — | >2000 |
| Afore-mentioned A compound | P-CONH$_2$ | >400 | >400 | >400 | >400 | >400 |

Note.- The numerical values in the table denote the amounts per unit body weight of the nitrofuran derivatives required for cure when the experiment was carried out using mice of body weight of about 20 grams and injecting thereinto abdominally the microorganism-containing solutions in amounts of 0.2 ml (the microorganism-containing solutions used being those in the cases of test microorganisms 1, 3 and 4 in which the microorganism culture liquids were diluted 10$^5$, 5 and 10$^2$ times, respectively, and in the case of test microorganism 2 that which was concentrated 2 times), after which the nitrofuran derivatives suspended in 5% gum arabic were forcedly administered orally followed by observation for one week.

As is apparent from the foregoing Table 1–4, the typical nitrofuran derivatives of this invention demonstrate excellent results with respect to their minimum growth inhibiting concentrations when used with the various microorganisms. Further, exceedingly satisfac- diseases of man caused by bacterial infections such as infections of either the alimentary canal or urinary tract by such bacteria as escherichia species, *Shigalla*, *Staphylococcus aureus* and *Streptococcus hemolyticus*.

Further, the invention nitrofuran derivatives are suitably used as a medicine of animals other than man in the prevention or cure of diseases of, say, chicken or swine infected by such pathogenic bacteria as, for example, salmonella species, *Escherichia coli*, staphylococcus species, pasteurella species and erysiperothris species, e.g., *Swine erysipelas*, and *Staphylomycosis* or *Salmonella purollum* of chicken.

Further, the invention nitrofuran derivatives are also suitable for use as a medicine for fish in the prevention or cure of infectious diseases resulting from infection by pathogenic bacteria such, for example, as *Aeromonas liquefaciens* and *Aerononas salmonicida; Vibrio anguillarum* and *Vibrio piscium; Chondrcoccus columporis;* or *Pasteurella piscicida*, e.g. *Pseudotuberculosis* (a disease of yellowtail caused by *Pasteurella piscicida*), scale protrusion disease (a disease of carp caused by *Aeromonas liquifaciens*), fin rot (a disease of eel caused by either *Aeromonas liquifaciens* or *Vibrio anguillarum*), and *Furunculosis* (a disease of rainbow trout caused by *Aeromonas salmonicida*).

There is provided according to the present invention a composition comprising as its active ingredient an effective amount of a nitrofuran derivative of the general formula

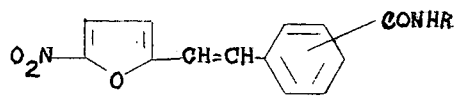

wherein R is as hereinabove defined, and a liquid or solid carrier or diluent.

In the case of a composition for human use, the nitrofuran derivative is contained in an amount of 5 – 90% by weight, and preferably 10 –80% by weight, based on the total weight of the composition.

The composition for use of animals other than man contains the nitrofuran derivative in an amount of 1–90% by weight, and preferably 5–80% by weight, based on the total weight of the composition.

On the other hand, the composition for fish use contains the nitrofuran derivative in an amount of 1–90% by weight, and preferably 5–80% by weight, based on the total weight of the composition.

The liquid or solid carriers or diluents include the customary nontoxic materials, for example, such solid vehicles, excipients and lubricants as glucose, lactose and sucrose, cornstarch, sodium carboxymethyl cellulose, ethyl cellulose and cellulose acetate, powdered gum tragacanth, gelatin, alginic acid, agar, stearic acid, sodium, calcium and magnesium stearates, sodium lauryl sulfate, polyvinyl pyrollidone, sodium citrate, and calcium carbonate and dicalcium phosphate; and such liquid carriers or diluents as water, water-miscible organic solvents (e.g. ethanol), sesame oil, groundnut oil, N,N-dimethyl-formamide and aqueous propylene glycol. Further, the composition can also be incorporated with nonionic and anionic emulsifiers (e.g. polyoxyethylene gatty alcohol ethers, alkyl sulfonates and arysulfonates), perfumes, flavoring agents and dyes.

The foregoing compositions can be made up in customary manner into such medicaments as tablets, granular preparations, enteric tablets, pills, capsules, powders, injectable solutions, suspensions and pastes.

In the case of man, the nitroguran derivative of the general formula I is administered as such or as a composition or a medicament such as above described (e.g. tablet, granular preparation, enteric tablet, pill, capsule or powder) continuously for several days from one to several times daily at a dosage of 5–50 mg/kg of body weight, and preferably 10–40 mg/kg of body weight. The amount administered can be suitably increased or decreased in accordance with the conditions of the disease.

In the case of animals other than man, the nitrofuran derivative can be administered orally or injected subcutaneously as such or as a composition or a medicament such as above described (e.g. tablet, granular preparation, pill, capsule, powder suspension or injectable solution) at a dosage of 5–100 mg/kg of body weight, and preferably 10–40 mg/kg of body weight. Further, the nitrofuran derivative can be administered by adding it to animal feeds at a concentration of 20–1000 ppm, and preferably 50–500 ppm.

On the other hand, in the case of fish, the nitrofuran derivative is administered as such or as a composition or medicament such as above described (e.g. aqueous solution, suspension, injection solution or paste) usually in a single dosage of 1–400 mg/kg of body weight of fish; and when orally administered, usually at a dosage of 1–10 mg/kg of body weight of fish, and when administered by injection, preferably at a dosage of 10–400 mg/kg of body weight of fish. Further, a medicinal bath prepared by dissolving in customary manner the nitrofuran derivative at a concentration of 0.1 – 50 ppm, and preferably 1 –20 ppm, in brine, seawater or fresh water can also be employed.

Therefore, there is provided according to the present invention a method of preventing or curing disorders caused by microorganisms, which method comprises administering to man, animals other than man, or fish a nitrofuran derivative of the general formula

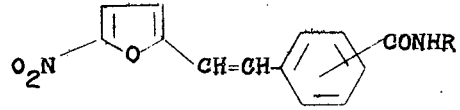

wherein R is as hereinbefore defined, in an effective amount thereof singly or as a mixture thereof with either a carrier or diluent; there also being provided animals other than man, or fish in which disorders caused by microorganisms have been prevented or cured by the use of the said nitrofuran derivative.

The following examples will further serve to illustrate the present invention.

EXAMPLE 1

2-Para-[2'-(5''-nitro-2''-furyl)-vinyl]-benzoylaminoethanol

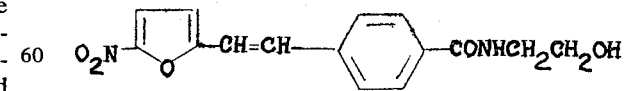

Five hundred ml of a monochlorobenzene solution containing 27.8 grams of para-[2-(5'-nitro-2'-furyl)-vinyl]-benzoyl chloride was added dropwise at below 20° C. to a mixture of 36.6 grams of 2-aminoethanol and 150 ml of water, followed by stirring for 30 minutes. When the precipitated crystals were filtered, water-washed and recrystallized from dilute methanol, 24 grams of the intended substance was obtained as orange-yellow crystals having a melting point of 183°–184° C.

| Elementary analysis: | C | H | N |
|---|---|---|---|
| Calcd. (%) for $C_{15}H_{14}N_2O_5$: | 59.60 | 4.67 | 9.27 |
| Found (%): | 59.47 | 4.58 | 9.13 |

EXAMPLE 2

2-Meta-[2'-(5''-nitro-2''-furyl)-vinyl]-benzoylaminoethanol

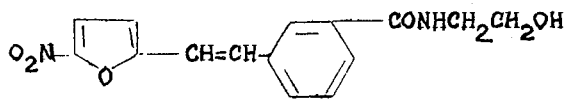

Example 1 was repeated but using 27.8 grams of meta-[2-(5'-nitro-2'-furyl)-vinyl]-benzoyl chloride instead of the acid chloride used therein to obtain 23 grams of the intended substance as orange-yellow crystals having a melting point of 194°–195° C.

| Elementary analysis: | C | H | N |
|---|---|---|---|
| Calcd. (%) for $C_{15}H_{14}N_2O_5$: | 59.60 | 4.67 | 9.27 |
| Found (%): | 59.52 | 4.46 | 9.15 |

EXAMPLE 3

Para-[2-(5'-nitro-2'-furyl)-vinyl]-benzoylhydroxylamine

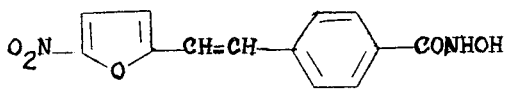

The reaction was operated exactly as in Example 1, except that 240 grams of an aqueous solution containing 19.8 grams of hydroxylamine was used instead of the aqueous 2-aminoethanol solution, after which the reaction product was recrystallized from dilute methyl Cellosolve to obtain 18.5 grams of the intended substance or yellow crystals having a melting point of 258° – 260° C. (decomposition).

| Elementary analysis: | C | H | N |
|---|---|---|---|
| Calcd. (%) for $C_{13}H_{10}N_2O_5$: | 56.93 | 3.68 | 10.22 |
| Found (%): | 56.86 | 3.72 | 10.03 |

EXAMPLE 4

3-Para-[2'-(5''-nitro-2''-furyl)-vinyl]-benzoylamino-1-propanol

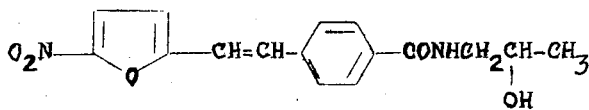

Example 1 was repeated but using 45 grams of 3-amino-1-propanol instead of 2-aminoethanol to obtain 25.7 grams of the intended substance as yellow-orange crystals having a melting point of 164.5°–166° C.

| Elementary analysis: | C | H | N |
|---|---|---|---|
| Calcd.(%) for $C_{16}H_{16}N_2O_5$: | 60.75 | 5.10 | 8.86 |
| Found (%): | 60.39 | 5.25 | 8.71 |

EXAMPLE 5

3-Para[2'-(5''-nitro-2''-furyl)-vinyl]-benzoylamino-2-propanol $$O_2N-\underset{O}{\boxed{\phantom{x}}}-CH=CH-\underset{}{\boxed{\phantom{x}}}-CONHCH_2\underset{OH}{\overset{|}{C}H}-CH_3$$

The experiment was operated exactly as in Example 1, except that 45 grams of 3-amino-2-propanol was used instead of 2-aminoethanol to obtain 25.5 grams of the intended substance as yellow-orange crystals having a melting point of 172.5°–173.5° C.

| Elementary analysis: | C | H | N |
|---|---|---|---|
| Calcd. (%) for $C_{16}H_{16}N_2O_5$: | 60.75 | 5.10 | 8.86 |
| Found (%): | 60.54 | 5.46 | 8.58 |

EXAMPLE 6

2-Para-[2'-(5''-nitro-2''-furyl)-vinyl]-benzoylamino-2-methyl-3-propanol

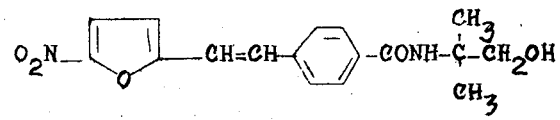

Example 1 was repeated but using 54 grams of 2-amino-2-methyl-3-propanol instead of 2-aminoethanol to obtain 27.3 grams of the intended substance as yellow crystals having a melting point of 138°–140° C.

| Elementary analysis: | C | H | N |
|---|---|---|---|
| Calcd. (%) for C$_{17}$H$_{18}$N$_2$O$_5$: | 61.81 | 5.49 | 8.48 |
| Found (%): | 61.77 | 5.53 | 8.32 |

EXAMPLE 7

2-Para-[2'-(5''-nitro-2''-furyl)-vinyl]-benzoylamino-2-methyl-1,3-propanediol

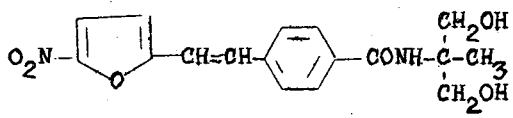

The reaction was operated exactly as in Example 1 but using 63 grams of 2-amino-2-methyl-1,3-propanediol instead of 2-aminoethanol followed by recrystallization of the resulting crystals from dilute methyl Cellosolve to obtain 28.4 grams of the intended substance as yellow crystals having a melting point of 185°–187° C. (decomposition).

| Elementary analysis: | C | H | N |
|---|---|---|---|
| Calcd. (%) for C$_{17}$H$_{18}$N$_2$O$_6$: | 58.95 | 5.24 | 8.09 |
| Found (%): | 59.12 | 5.13 | 7.87 |

EXAMPLE 8

2-para-[2'-(5''-nitro-2''-furyl)-vinyl]-benzoylamino-2-hydroxymethyl-1,3-propanediol

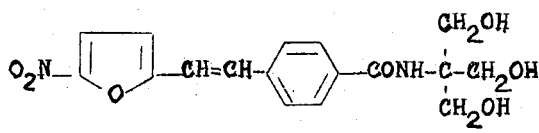

The reaction was operated exactly as in Example 1, except that 73 grams of 2-amino-2-hydroxymethyl-1,3-propanediol was used instead of 2-aminoethanol, after which the resulting crystals were recrystallized from dilute methyl Cellosolve to obtain 29 grams of the intended substance as yellow crystals having a melting point of 196°–198° C. (decomposition).

| Elementary analysis: | C | H | N |
|---|---|---|---|
| Calcd. (%) for C$_{17}$H$_{18}$N$_2$O$_7$: | 56.35 | 5.01 | 7.73 |
| Found (%): | 56.13 | 5.20 | 7.48 |

EXAMPLE 9

3-Para-[2'-(5''-nitro-2''-furyl)-vinyl]-benzoylamino-1,2-propanediol

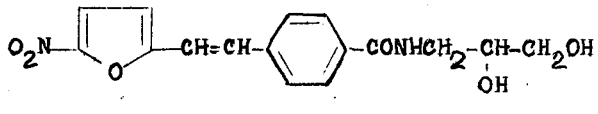

The reaction was carried out using 40 grams of 3-amino-1,2-propanediol instead of the 2-aminoethanol used in Example 1, but otherwise the experiment was carried out as described therein. The product became oily in character and separated from the solvent layer. When this oily product was recrystallized from dilute methyl Cellosolve, 20.8 grams of the intended substance was obtained as yellow crystals having a melting point of 116°–168° C. (decomposition).

| Elementary analysis: | C | H | N |
|---|---|---|---|
| Calcd. (%) for C$_{16}$H$_{16}$N$_2$O$_5$: | 57.83 | 4.85 | 8.43 |
| Found (%): | 57.66 | 4.98 | 8.27 |

EXAMPLE 10

2-Para-[2'-(5''-nitro-2''-furyl)-vinyl]-benzoylamino-ethylmercaptan

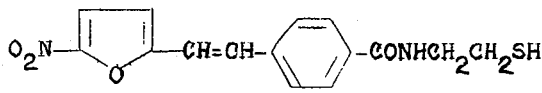

The reaction was operated exactly as in Example 1, except that 46 grams of 2-aminoethyl mercaptan was used instead of 2-aminoethanol. The resulting crystals were filtered off, washed in methanol and thereafter dried to obtain 24.7 grams of the intended substance as yellow crystals having a melting point of 212°–215° C. (decomposition).

| Elementary analysis: | C | H | N |
|---|---|---|---|
| Calcd. (%) for C$_{15}$H$_{14}$N$_2$O$_4$S: | 56.60 | 4.43 | 8.80 |
| Found (%): | 56.43 | 4.38 | 8.72 |

EXAMPLE 11

2-Para-[2'-(5''-nitro-2''-furyl)-vinyl]-benzoylaminoethoxy-2-ethanol

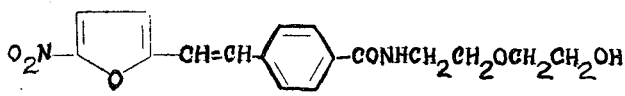

The reaction was operated as in Example 1 but using 63 grams of 2-(2-aminoethoxy)-ethanol instead of 2-aminoethanol, after which the resulting crystals were recrystallized from dilute methyl Cellosolve to obtain 29.6 grams of the intended substance as yellow acicular crystals having a melting point of 151°–152° C.

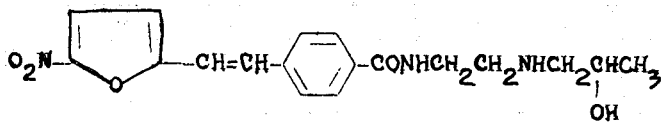

| Elementary analysis: | C | H | N |
|---|---|---|---|
| Calcd. (%) for C₁₇H₁₈N₂O₆: | 58.95 | 5.24 | 8.09 |
| Found (%): | 58.78 | 5.15 | 8.32 |

EXAMPLE 12

3-Para-[2'-(5''-nitro-2''-furyl)-vinyl]-benzoylamino-n-propylmethyl ether

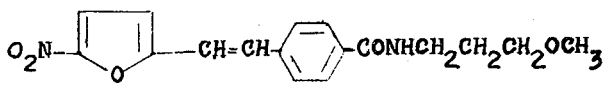

The reaction was operated as in Example 1 but using 54 grams of 3-amino-n-propylmethyl ether instead of 2-aminoethanol, after which the resulting crystals were recrystallized from dilute methyl Cellosolve the obtain 28.2 grams of the intended substance as yellow sheet-like crystals having a melting point of 169°–172° C.

| Elementary analysis: | C | H | N |
|---|---|---|---|
| Calcd. (%) for C₁₇H₁₈N₂O₅: | 61.81 | 5.49 | 8.48 |
| Found (%): | 62.03 | 5.26 | 8.33 |

EXAMPLE 13

2-[2'-Para- 2''-(5''-nitro-2'''-furyl)-vinyl -benzoylaminoethylamino]-1-ethanol

Example 1 was repeated but using 68 grams of hydroxyethylaminoethylamine instead of 2-aminoethanol to obtain 26.2 grams of the intended substance as yellow crystals having a melting point of 208°–209° C.

| Elementary analysis: | C | H | N |
|---|---|---|---|
| Calcd. (%) for C₁₇H₁₉N₃O₅: | 59.12 | 5.55 | 12.17 |
| Found (%): | 59.40 | 5.46 | 12.26 |

EXAMPLE 14

1-[2'-Para- 2''-(5'''-nitro-2'''-furyl)-vinyl -benzoylaminoethylamino]-2-propanol Example 1 was repeated but using 77 grams of 2-hydroxypropylaminoethylamine instead of 2-aminoethanol to obtain 26.9 grams of the intended substance as yellow crystals having a melting point of 225.5°–226° C.

| Elementary analysis: | C | H | N |
|---|---|---|---|
| Calcd. (%) for C₁₈H₂₁N₃O₅: | 60.16 | 5.89 | 11.69 |
| Found (%) | 59.87 | 5.74 | 11.73 |

EXAMPLE 15

Para-[2-(5'-nitro-2'-furyl)-vinyl]-benzoylglycine

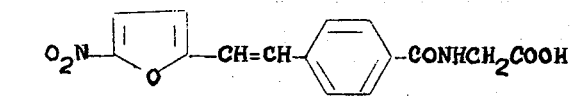

7.5 grams of glycine was dissolved in 300 ml of 1 N sodium hydroxide solution, after which a liquid mixture of 24 grams of para-[2-(5'-nitro-2'-furyl)-vinyl]-benzoyl chloride and 400 ml of dioxane was added with stirring while the mixture was being cooled with ice. After continuing the reaction for 1.5 hours at 10°–15° C., the reaction mixture was neutralized with a 1 N citric acid solution followed by filtering off the precipitated crystals. When these crystals were recrystallized from acetic acid, 7.2 grams of the intended substance was obtained as yellow flaky crystals having a melting point of 224°–228° C.

| Elementary analysis: | C | H | N |
|---|---|---|---|
| Calcd. (%) for C₁₅H₁₂N₂O₆: | 56.96 | 3.82 | 8.86 |
| Found (%): | 56.85 | 3.70 | 8.60 |

EXAMPLE 16

Para-[2-(5'-nitro-2'-furyl)-vinyl]-N-benzoylglycine amide

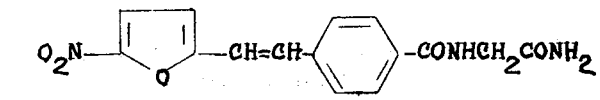

4.4 Grams of glycine amide hydrochloride and 11.2 ml of triethylamine were added to 200 ml of chloroform, to which mixture was then added a liquid mixture of 11 grams of para -[2-(5'-nitro-2'-furyl)-vinyl]-benzoyl chloride and 100 ml of tetrahydrofuran with stirring while cooling the mixture with ice. The stirring was continued for 30 minutes while being cooled and for a further 2 hours at room temperature, after which the separated crystals were filtered off. The so obtained crystals were dissolved in dimethylformamide, and the small quantity of insolubles were filtered off. The filtrate was then dried under reduced pressure. When the resulting residue was recrystallized from a liquid mixture of methyl Cellosolve, ethyl ether and n-hexane, 2.4 grams of the intended substance was obtained as yellow crystals having a melting point of 239°–243° C.

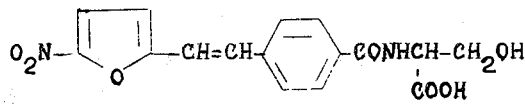

In a solution of 3.7 grams of sodium hydrogencarbonate in 120 ml of water was dissolved 4.6 grams of L-serine, to which solution was then added incrementally in small amounts 11 grams of para-[2-(5'-nitro-2'-furyl)-vinyl]-benzoyl chloride with stirring at 5° C. After agitation for 2 hours at 5° C. and one hour at room temperature, the mixture was neutralized with 1 N hydrochloric acid, after which the precipitated crystals were filtered off and water-washed. These crystals were then dissolved in dioxane with heating, and the insolubles were filtered off. When the filtrate, after concentration, was recrystallized from n-hexane, 3.8 grams of the intended substance was obtained as yellow crystals having a melting point of 213°–218° C.

| Elementary analysis: | C | H | N |
|---|---|---|---|
| Calcd. (%) for $C_{15}H_{11}N_3O_5$: | 57.14 | 4.16 | 13.33 |
| Found (%): | 56.97 | 4.16 | 12.94 |

| Elementary analysis: | C | H | N |
|---|---|---|---|
| Calcd. (%) for $C_{16}H_{14}N_2O_7$: | 55.49 | 4.08 | 8.09 |
| Found (%): | 55.68 | 4.22 | 7.87 |

EXAMPLE 17

Para-[2-(5'-nitro-2'-furyl)-vinyl]-N-benzoylasparagine

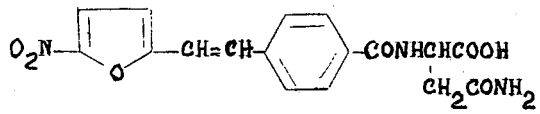

Twelve grams of asparagine was dissolved in 100 ml of 1.6 N sodium hydroxide solution, to which was then added a liquid mixture of 11 grams of para-[2-(5'-nitro-2'-furyl)-vinyl]-benzoyl chloride and 50 ml of dioxane with stirring and while cooling the mixture with ice. The stirring was continued while being cooled with ice for 30 minutes, and the mixture was then neutralized with 1 N hydrochloric acid, after which the precipitated crystals were filtered off and water-washed. This was followed by dissolving the so obtained crystals in hot methyl Cellosolve and filtering off the small amount of insolubles. When the filtrate was added an ethyl ether- n-hexane liquid mixture and recrystallized, 9 grams of the intended was obtained as yellow crystals having a melting point of 201° – 204° C.

EXAMPLE 19

Para-[2-(5'-nitro-2'-furyl)-vinyl]-N-benzoylserine amide

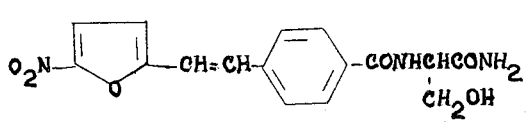

13.9 Grams of serine amide and 28 ml of triethylamine were dissolved in 70 ml of chloroform, and while cooling the mixture with ice 25.9 grams of para-[2-(5'-nitro-2'-furyl)-vinyl]-benzoyl chloride was promptly added with stirring. The reaction was then carried out for 2 hours under ice-cooled conditions and for 30 minutes at 40° C., after which the precipitated crystals were filtered off and washed in chloroform. The crystals were then dissolved in hot methyl Cellosolve, and the insolubles were separated by filtration. This was followed by cooling the filtrate and filtering off the crystals. When these crystals were then recrystallized from methyl Cellosolve, 14 grams of the intended substance was obtained as yellow acicular crystals having a melting point of 237°–239° C.

| Elementary analysis: | C | H | N |
|---|---|---|---|
| Calcd. (%) for $C_{17}H_{15}N_3O_7$: | 54.69 | 4.05 | 11.26 |
| Found (%): | 55.10 | 4.04 | 11.08 |

| Elementary analysis: | C | H | N |
|---|---|---|---|
| Calcd. (%) for $C_{16}H_{15}N_3O_6$: | 55.65 | 4.38 | 12.17 |
| Found (%) | 55.72 | 4.56 | 12.34 |

EXAMPLE 18

Para-[2-(5'-nitro-2'-furyl)-vinyl]-benzoylserine

EXAMPLE 20

Para-[2-(5'-nitro-2'-furyl)-vinyl]-N (α)-benzoylarginine

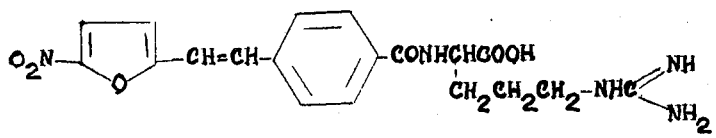

To a suspension in 75 ml of water of 18.9 grams of sodium hydrogencarbonate was added 12.6 grams of arginine hydrochloride, to which suspension was then added at room temperature 16.5 grams of para-[2-(5'-furyl)-vinyl]-benzoyl chloride over a 30-minute period with stirring. After stirring this mixture for 2 hours at room temperature, its pH value was adjusted to 6 with acetic acid and ammonia. The precipitate was then filtered off, water-washed and dried, followed by dissolving it in methyl Cellosolve with heating and filtering off the insolubles. The filtrate was then cooled, and the precipitated crystals were collected and recrystallized from methyl Cellosolve. When these crystals, after washing with hot ammonia water of pH 8.5, were again recrystallized from methyl Cellosolve, 1.8 grams of the intended substance was obtained as yellow needle crystals having a melting point of 187°–191° C.

| Elementary analysis: | C | H | N |
|---|---|---|---|
| Calcd. (%) for | | | |
| $C_{19}H_{21}N_5O_6$: | 54.93 | 5.10 | 16.86 |
| Found (%): | 55.21 | 5.05 | 17.02 |

EXAMPLE 21

2-Ortho-[2'-(5''-nitro-2''-furyl)-vinyl]-benzoylaminoethanol

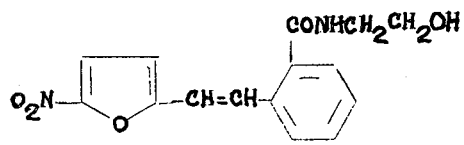

Example 1 was repeated but using 27.8 grams of ortho-[2-(5'-nitro-2'-furyl)-vinyl]-benzoyl chloride instead of the acid chloride used therein to obtain 22.5 grams of the intended substance as orange-yellow crystals having a melting point of 188°–189° C.

| Elementary analysis: | C | H | N |
|---|---|---|---|
| Calcd. (%) for | | | |
| $C_{15}H_{14}N_2O_5$: | 59.60 | 4.67 | 9.27 |
| Found (%): | 59.88 | 4.51 | 9.36 |

EXAMPLE 22

Ortho-[2-(5'-nitro-2'-furyl)-vinyl]-benzoylhydroxylamine

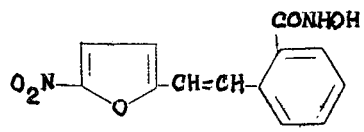

Example 3 was repeated but using 32.2 grams of ortho-[2-(5'-nitro-2'-furyl)-vinyl]-benzoyl bromide instead of the acid chloride used therein to obtain 17.7 grams of the intended substance as yellow crystals having a melting point of 267°–269° C. (decomposition).

| Elementary analysis: | C | H | N |
|---|---|---|---|
| Calcd. (%) for | | | |
| $C_{13}H_{10}N_2O_5$: | 56.93 | 3.68 | 10.22 |
| Found (%): | 56.97 | 3.85 | 10.16 |

EXAMPLE 23

2-Meta-[2'-(5''-nitro-2''-furyl)-vinyl]-benzoylaminoethyl mercaptan

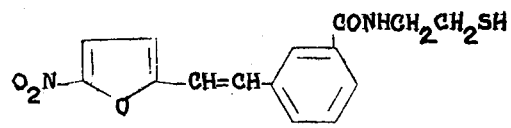

Example 10 was repeated but using 32.2 grams of meta-[2-(5'-nitro-2'-furyl)-vinyl]-benzoyl bromide instead of the acid chloride used therein to obtain 23.5 grams of the intended substance as yellow crystals having a melting point of 223°–224° C. (decomposition).

| Elementary analysis: | C | H | N |
|---|---|---|---|
| Calcd. (%) for | | | |
| $C_{15}H_{14}N_2O_4S$: | 56.60 | 4.43 | 8.80 |
| Found (%): | 56.79 | 4.58 | 8.57 |

EXAMPLE 24

Ortho-[2-(5'-nitro-2'-furyl)-vinyl]-N-benzoylglycine

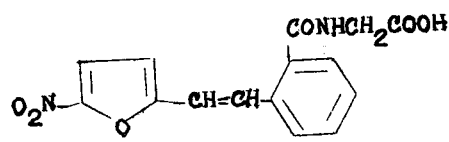

Example 15 was repeated but using 24 grams of ortho-[2-(5'-nitro-2'-furyl)-vinyl]-venzoyl chloride instead of the acid chloride used therein to obtain 6.7 grams of the intended substance as yellow flaky crystals having a melting point of 232°–234° C.

| Elementary analysis: | C | H | N |
|---|---|---|---|
| Calcd. (%) for | | | |
| $C_{15}H_{12}N_2O_6$: | 56.96 | 3.82 | 8.86 |
| Found (%): | 57.22 | 3.91 | 8.58 |

EXAMPLE 25

Meta-[2-(5'-nitro-2'-furyl)-vinyl]-N-benzoylasparagine

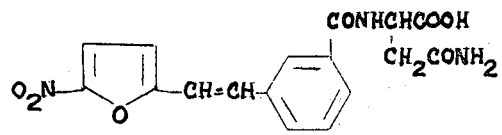

Example 17 was repeated but using 11 grams of meta-[2-(5'-nitro-2'-furyl)-vinyl]-benzoyl chloride instead of the acid chloride used therein to obtain 8.2 grams of the intended substance as yellow crystals having a melting point of 209°–213° C.

| Elementary analysis: | C | H | N |
|---|---|---|---|
| Calcd. (%) for | | | |
| $C_{17}H_{15}N_3O_7$: | 54.69 | 4.05 | 11.26 |
| Found (%): | 54.87 | 4.12 | 11.50 |

EXAMPLE 26

2-Para-[2'-(5''-nitro-2''-furyl)-vinyl]-benzoylaminoethanesulfonic acid

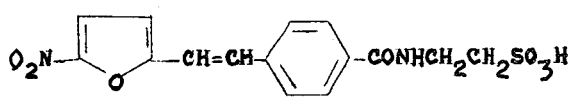

12.5 Grams of 2-aminoethanesulfonic acid was added to a solution of 8 grams of sodium hydroxide in 120 ml of water, to which was further added dropwise with stirring 400 ml of a monochlorobenzene solution containing dissolved therein 27.4 grams of para-[2-(5'-nitro-2'-furyl)-vinyl]-benzoyl chloride, the dropping being carried out while cooling the mixture to below 20° C. Next, after reacting the mixture for 30 minutes, the precipitated crystals were filtered off, water-washed and then neutralized by adding the crystals incrementally in dilute hydrochloric acid. The resulting crystals were filtered off and washed in water. When these crystals were recrystallized form dilute methyl Cellosolve, 25.6 grams of the intended substance was obtained as yellow crystals having a melting point above 280° C.

| Elementary analysis: | C | H | N |
|---|---|---|---|
| Calcd. (%) for | | | |
| $C_{15}H_{14}N_2O_7S$: | 49.18 | 3.85 | 7.65 |
| Found (%): | 48.79 | 3.56 | 7.94 |

EXAMPLE 27

Para-[2-(5'-nitro-2'-furyl)-vinyl]-N(α)-benzoyllysine

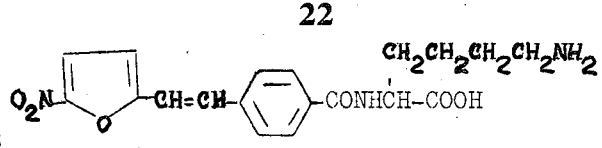

11.7 Grams of N(ε)-benzylidenelysine was dissolved in a liquid mixture of 75 ml of 1N sodium hydroxide, 2.5 grams of sodium hydrogencarbonate and 50 ml of water, to which was then added with stirring 13.7 grams of para-[2-(5'-nitro-2'-furyl)-vinyl]-benzoyl chloride while cooling the mixture with ice. Agitation of the mixture was then carried out for 1.5 hours at 2°–3° C. and then for 20 minutes at room temperature. Next, after adding 12 ml of concentrated hydrochloric acid, the mixture was stirred for a further 40 minutes at 45° C., after which the pH of the mixture was adjusted to 6 with 1 N sodium hydroxide, and the mixture was filtered off, followed by washing in water and methanol and drying. The resulting product was dissolved in methyl Cellosolve with heating, and the insolubles were filtered off. The filtrate was cooled to −10° C., and the precipitate was filtered off, washed with ethyl ether and dried to obtain the intended substance as yellow crystals having a melting point of 154°–156° C.

| Elementary analysis: | C | H | N |
|---|---|---|---|
| Calcd. (%) | | | |
| $C_{19}H_{21}N_3O_6$: | 58.91 | 5.46 | 10.85 |
| Found (%) | 58.78 | 5.39 | 11.0 |

EXAMPLE 28

Sodium 2-para-[2'-(5''-nitro-2''-furyl)-vinyl]-benzoylaminoethanesulfonate

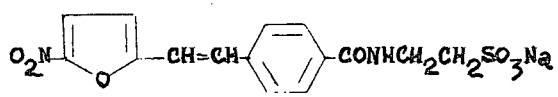

12.5 Grams of 2-aminoethanesulfonic acid was added to a solution of 8 grams of sodium hydroxide in 120 ml of water, to which was then added dropwise with stirring 400 ml of a monochlorobenzene solution having dissolved therein 27.4 grams of para-[2-(5'-nitro-2'-furyl)-vinyl]-benzoyl chloride, the dropping being carried out while cooling the mixture to below 20° C. Next, after reacting the mixture for 30 minutes, the precipitated crystals were filtered off and water-washed. When the so obtained crystals were recrystallized from dilute methanol, 31.1 grams of the intended substance was obtained a yellow crystals having a melting point of above 300° C.

| Elementary analysis: | C | H | N |
|---|---|---|---|
| Calcd. (%) for | | | |
| $C_{15}H_{13}N_2O_7SNa$: | 46.39 | 3.37 | 7.21 |
| Found (%): | 46.10 | 3.51 | 7.06 |

EXAMPLE 29

Potassium ortho-[2-(5'-nitro-2'-furyl)-vinyl]-vinyl-N-benzoylglycine

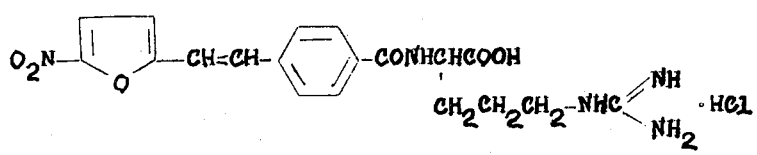

A solution of 1.1 grams of potassium hydroxide in 10 ml of methanol was added to a solution of 6.3 grams of ortho-[2-(5'-nitro-2'-furyl)-vinyl]-N-benzoylglycine in 250 ml of methanol, and the mixture was stirred for 30 minutes. On concentration of this mixture under reduced pressure, 6.5 grams of the intended substance was obtained as yellow crystals having a melting point above 280° C.

| Elementary analysis: | C | H | N |
|---|---|---|---|
| Calcd. (%) for $C_{15}H_{11}N_2O_6K$: | 50.84 | 3.13 | 7.91 |
| Found (%): | 51.12 | 3.06 | 7.63 |

EXAMPLE 30

Para[2-(5'-nitro-2'-furyl)-vinyl]-N($\alpha$)-benzoylarginine hydrochloride

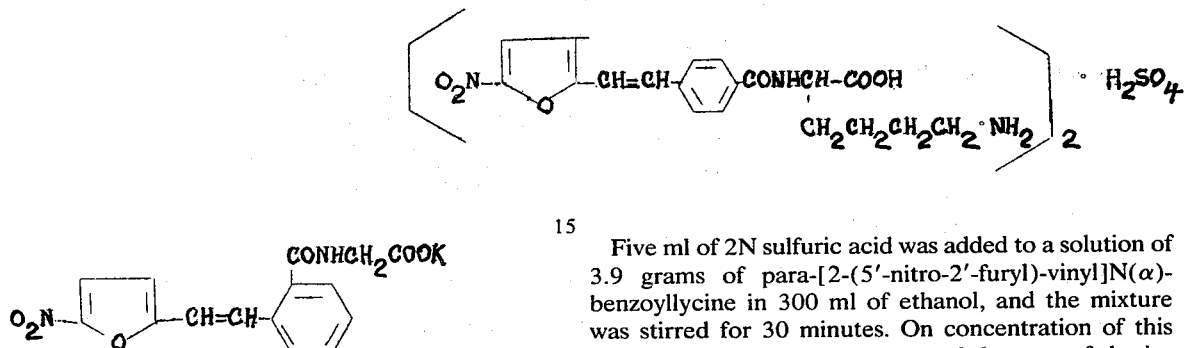

Five ml of 2N hydrochloric acid was added to a solution of 4.1 grams of para-[2-(5'-nitro-2'-furyl)vinyl]-N($\alpha$)-benzoylarginine in 300 ml of ethanol, and the mixture was stirred for 30 minutes. On concentration of the mixture under reduced pressure, 3.7 grams of the intended substance was obtained as yellow crystals having a melting point above 250° C.

| Elementary analysis: | C | H | N |
|---|---|---|---|
| Calcd. (%) for $C_{19}H_{22}N_5O_6Cl$: | 50.50 | 4.91 | 15.50 |
| Found (%): | 50.22 | 4.76 | 15.73 |

EXAMPLE 31

Para-[2-(5'-nitro-2'-furyl)-vinyl]-N($\alpha$)-benzoyllycine sulfate

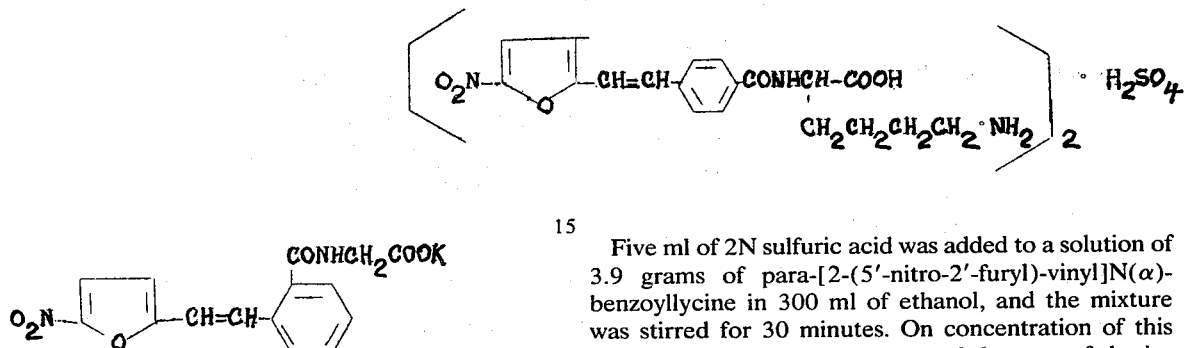

Five ml of 2N sulfuric acid was added to a solution of 3.9 grams of para-[2-(5'-nitro-2'-furyl)-vinyl]N($\alpha$)-benzoyllycine in 300 ml of ethanol, and the mixture was stirred for 30 minutes. On concentration of this mixture under reduced pressure, 3.6 grams of the intended substance was obtained as yellow crystals having a melting point above 280° C.

| Elementary analysis: | C | H | N |
|---|---|---|---|
| Calcd. (%) for $C_{38}H_{44}N_6O_{16}S$: | 52.29 | 5.08 | 9.63 |
| Found (%): | 52.57 | 5.12 | 9.36 |

EXAMPLE 32

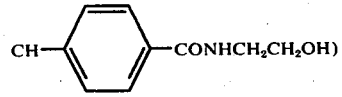

| | Grams |
|---|---|
| Compound of Example 1 ($O_2N$—CH—CH—CONHCH$_2$CH$_2$OH) | 1250 |
| Starch | 60 |
| Lactose | 1630 |
| Magnesium stearate | 60 |

Granules were prepared from a mixture of the foregoing ingredients in customary manner, using a liquid 5% starch paste as the binding agent, following which the resulting granules were made into 10,000 tablets.

EXAMPLE 33

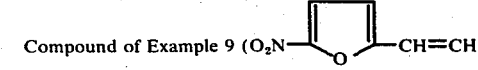
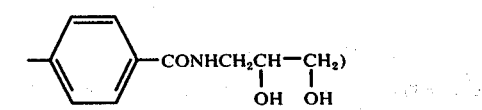

| | Grams |
|---|---|
| Compound of Example 9 ($O_2N$—CH=CH—CONHCH$_2$CH—CH$_2$) OH OH | 2500 |
| Starch | 60 |
| Lactose | 410 |

-continued

| | |
|---|---|
| Calcium stearate | 30 |

The foregoing ingredients were treated in customary manner as described in the previous example to obtain 10,000 tablets, which tablets were then coated in customary manner with a solution consisting of

| | |
|---|---|
| Cellulose acetate phthalate | 10.0% |
| Acetone | 87.0% |
| Diethyl phthalate | 3.0% | thus preparing enteric tablets.

EXAMPLE 34

Mice of body weight about 20 grams were used, and 0.2 ml of a culture liquid obtained by cultivating *Erysiperothrix rhusiopatiae Agata* for 24 hours at 37° C. in a 10% calf serum TSB added culture medium (amount of inoculated germs $4.0 \times 10^7$) was injected abdominally. Next, these mice were either forcedly administered orally or injected subcutaneously in the abdominal region with the hereinafter indicated nitrofuran derivatives suspended in 5% aqueous gum arabic, after which the mice were observed for 7 days. The amounts of nitrofuran derivatives required for the cure are shown in Table 5.

Table 5

$ED_{50}$ When Used With *Erysiperothrix rhusiopatiae* (mg/kg)

| Compound | | Oral Administration | Subcutaneous Injection (mg/kg body wt.) |
|---|---|---|---|
| Example | —CONHR | | |
| 1 | p-CONH CH₂CH₂OH | 21.8 | 50.0 |
| 9 | p-CONH CH₂CH—CH₂ \| \| OH OH | 25.5 | 42.1 |

EXAMPLE 35

A culture liquid obtained by cultivating *Salmonella pullorum* NIAH 5159 in a YCCB culture medium for 20 hours at 37° C. was injected into the cloaca of 2-day-old chicks at the rate of 0.2 ml per chick. Nitrofuran derivatives in total amounts indicated below were then mixed with the feed, and the so mixed feed was fed to the chicks for 7 days. The chicks were then sacrificed, and the liver and/or spleen were homogenized, following which the product was cultivated for 48 hours at 37° C. in a YCCB culture medium in customary manner. Whether or not there was an increase in the germs was then judged with the results shown in Table 6. The expression, "rate of germ isolation" used in the table has the following meaning. For instance, the value 4/10 means the germs were isolated from four out of the ten chicks submitted to the test.

Table 6

Effectiveness in Preventing Infection by *Salmonella pullorum*

| Compound | | Amount Administered ppm | Rate of Germ Isolation |
|---|---|---|---|
| Example | —CONHR | | |
| 1 | p-CONH CH₂CH₂OH | 50 | 4/10 |
| | | 100 | 4/10 |
| | | 200 | 3/10 |
| | | 400 | 2/10 |
| | | 800 | 0/10 |
| 9 | p-CONH CH₂CH—CH₂ \| \| OH OH | 50 | 4/10 |
| | | 100 | 4/10 |
| | | 200 | 3/10 |
| | | 400 | 2/10 |
| | | 800 | 1/10 |
| Control | | | 8/10 |

EXAMPLE 36

A culture liquid obtained by cultivation of *Staphlococcus aureus* Kawanabe II for 20 hours at 37° C. in a heart infusion culture medium was injected intravenously into 3-week-old chicks at the rate of 0.2 ml per chick. Nitrofuran derivatives mixed in amounts indicated below in the feeds were then fed these chicks for two weeks. The rate of chicks dying during this time were determined with the results shown in Table 7. In the table the expression, "death rate" has the following meaning. For instance, the value 3/9 denotes that three out of the nine chicks submitted to the test died.

Table 7

Curative Effects on Staphlomycosis of Fowl

| Compound | | Amount Administered ppm | Death Rate |
|---|---|---|---|
| Example | —CONHR | | |
| 1 | p-CONH CH₂CH₂OH | 50 | 3/9 |
| | | 100 | 2/9 |
| | | 200 | 2/9 |
| | | 400 | 2/9 |
| | | 800 | 1/9 |
| 9 | p-CONH CH₂CH—CH₂ \| \| OH OH | 50 | 3/9 |
| | | 100 | 2/9 |
| | | 200 | 2/9 |
| | | 400 | 2/9 |
| | | 800 | 2/9 |
| Control | | | 9/9 |

EXAMPLE 37

In raising young yellowtail of a body length about 10–15 cm, since a disease seeming to be vibroid ulcers started to appear, 90 of the fishes were collected and divided into three groups. The first group of 30 fishes were reared as heretofore practiced with no change. On the other hand, the second and third groups of 30 fishes were placed for 10 minutes in respectively medicinal baths containing seawater solutions of 10 ppm of the compound of Example 1

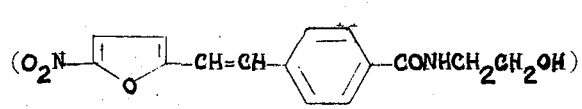

$(O_2N\text{—furan—}CH=CH\text{—phenyl—}CONHCH_2CH_2OH)$ and the compound of Example 9

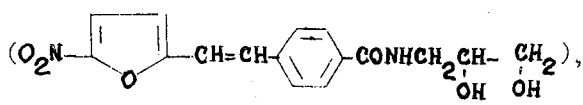

and the aminoalkyl portion of which contains 1–2 carbon atoms, alkoxyalkyl, the alkoxy portion of which contains 1–3 carbon atoms and the alkyl portion of which contains 1–3 carbon atoms, —CH$_2$CONH$_2$ and $$-\underset{\underset{CONH}{|}}{CH}-CH_2OH.$$

4. A nitrofuran derivative of claim 1 having the formula

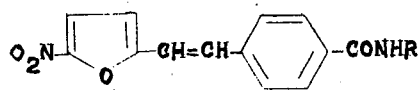

wherein R is as defined in claim 1.

5. A nitrofuran derivative of claim 1 having the general formula

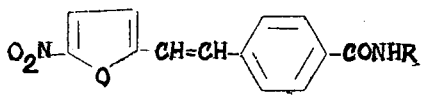

wherein R is as defined in claim 1.

6. A nitrofuran derivative of claim 2 having the general formula

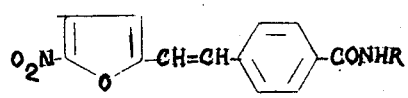

wherein R is as defined in claim 2.

7. A nitrofuran derivative of claim 3 having the general formula

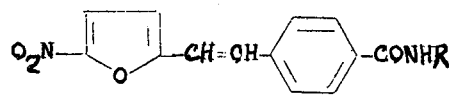

wherein R is as defined in claim 3.

8. 2-para-[2'-(5''-nitro-2''-furyl)-vinyl]-benzoylamino-ethanol,
9. 2-meta-[2'-(5''-nitro-2''-furyl)-vinyl]-benzoylamino-ethanol.
10. 3-para-[2'-(5''-nitro-2''-furyl)-vinyl]-benzoylamino-2-propanol.
11. 2-para-[2'-(5''-nitro-2''-furyl)-vinyl]-benzoylamino-2-methyl-3-propanol.
12. 3-para-[2'-(5''-nitro-2''-furyl)-vinyl]-benzoylamino-1,2-propanediol.
13. 2-para-[2'-(5''-nitro-2''-furyl)-vinyl]-benzoylaminoethoxy-2-ethanol.
14. Para-[2-(5'-nitro-2'-furyl)-vinyl]-N-benzoylglycine amide.
15. Para-[2-(5'-nitro-2'-furyl)-vinyl]-N-benzoylserine amide.
16. A nitrofuran derivative selected from the group consisting of:

following which the respective groups of fishes were returned to normal seawater where they were reared for a further 20 days. The number of fishes surviving in the case of the first group was three fishes, whereas in the case of the second and third groups, the numbers of fishes surviving were 26 and 25 fishes, respectively.

We claim:
1. A nitrofuran derivative having the formula

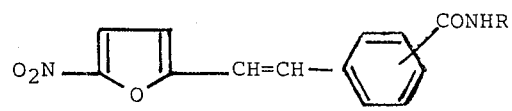

wherein R is a member selected from the group consisting of hydroxyl, hydroxyalkyl containing 1 to 5 hydroxyl groups, hydroxyalkoxyalkyl, hydroxyalkylaminoalkyl, alkoxyalkyl, $$\underset{\underset{CH-CH-COOH}{|}}{CH_2CH_2CH_2CH_2NH_2}, -CH_2COOH, -CH_2CONH_2,$$

$$-\underset{\underset{CH_2CONH_2}{|}}{CHCHCOOH}, -\underset{\underset{COOH}{|}}{CH}-CH_2OH, -\underset{\underset{CONH}{|}}{CH}-CH_2OH$$

and $-\underset{\underset{CH_2CH_2CH_2-NHC\overset{\diagdown NH_2}{\diagup NH}}{|}}{CHCOOH}$, said alkyl and alkoxy radicals of said groups having 1 to 6 carbon atoms; said CONHR group being in the para or meta position.

2. A nitrofuran derivative of claim 1 wherein R is a member selected from the group consisting of hydroxyl, hydroxyalkyl containing 1–3 hydroxyls, hydroxy alkoxyalkyl, hydroxyalkylaminoalkyl, alkoxyalkyl, $$-\underset{\underset{CH_2CH_2CH_2-NHC\overset{\diagdown NH_2}{\diagup NH}}{|}}{CHCOOH}, -\underset{\underset{CH_2CONH_2}{|}}{CHCHCOOH},$$

$$-CH_2COOH, CH_2CH_2CH_2CH_2NH_2, \text{ and } -\underset{\underset{COOH}{|}}{CH}-CH_2OH;$$
$$-\underset{}{CH}-CH-COOH$$

the alkyl and alkoxy radicals of which group having 1–4 carbon atoms.

3. A nitrofuran derivative of claim 1 wherein R is a group selected from the class consisting of hydroxyl, hydroxyalkyl containing 1–3 hydroxyls, the alkyl portion of which contains 1–4 carbon atoms, hydroxyalkoxyalkyl, the alkyl portion of which contains 1–2 carbon atoms and the alkoxy portion of which contains 1–3 carbon atoms, hydroxyalkylaminoalkyl, the hydroxyalkyl portion of which contains 1–3 carbon atoms 2-para-[2'-(5''-nitro-2''-furyl)-vinyl]-benzoylamino-2-methyl-1,3-propanediol;
2-para-[2'-(5''-nitro-2''-furyl)-vinyl]-benzoylamino-2-hydroxymethyl-1,3-propanediol;
3-para-[2'-(5''-nitro-2''-furyl)-vinyl]-benzoylamino-n-propylmethyl ether;
2-[2'-para-(2''-(5'''-nitro-2'''-furyl)-vinyl)-benzoylaminoethylamino]-1-ethanol;
1-[2'-para-(2''-(5'''-nitro-2'''-furyl)-vinyl]-benzoylamino-2-propanol;

para-[2-(5'-nitro-2'-furyl)-vinyl]-benzoylglycine;
para-[2-(5'-nitro-2'-furyl)-vinyl]-N-benzoylasparagine;
para-[2-(5'-nitro-2'-furyl)-vinyl]-benzoylserine;
para-[2-(5'-nitro-2'-furyl)-vinyl]-N-($\alpha$)-benzoylarginine; and
meta-[2-(5'-nitro-2'-furyl)-vinyl]-N-benzoylasparagine.

* * * * *